US006525033B1

(12) United States Patent
Schinazi et al.

(10) Patent No.: US 6,525,033 B1
(45) Date of Patent: Feb. 25, 2003

(54) NUCLEOSIDES WITH ANTI-HEPATITIS B VIRUS ACTIVITY

(75) Inventors: Raymond F. Schinazi, Decatur, GA (US); Jean-Pierre Sommadossi, Birmingham, AL (US); Gilles Gosselin, Montpellier (FR); Jean-Louis Imbach, Montpellier (FR)

(73) Assignees: Emory University, Atlanta, GA (US); University of Alabama Research Foundation, Inc., Birmingham, AL (US)

( * ) Notice: Subject to any disclaimer, the term of this patent is extended or adjusted under 35 U.S.C. 154(b) by 0 days.

(21) Appl. No.: 09/447,067

(22) Filed: Nov. 22, 1999

Related U.S. Application Data

(63) Continuation of application No. 08/829,748, filed on Mar. 31, 1997, now Pat. No. 5,990,093, which is a continuation of application No. 08/587,598, filed on Dec. 22, 1995, now abandoned, which is a continuation of application No. 08/320,461, filed on Oct. 7, 1994, now abandoned, which is a continuation of application No. 08/119,470, filed on Sep. 10, 1993, now abandoned.

(51) Int. Cl.$^7$ .......................... A61K 31/70; C07H 19/16
(52) U.S. Cl. ...................... 514/47; 536/26.7; 536/27.14
(58) Field of Search ........................... 514/47; 536/26.7, 536/27.14

(56) References Cited

U.S. PATENT DOCUMENTS

| | | |
|---|---|---|
| 4,000,137 A | 12/1976 | Dvonoch et al. |
| 4,336,381 A | 6/1982 | Nagata et al. |
| 4,818,538 A | 4/1989 | Rideout et al. |
| 4,861,759 A | 8/1989 | Mitsuya et al. |
| 4,879,277 A | 11/1989 | Mitsuya et al. |
| 4,900,828 A | 2/1990 | Belica et al. |
| 4,916,122 A | 4/1990 | Chu et al. |
| 4,963,533 A | 10/1990 | de Clerq et al. |
| 5,041,449 A | 8/1991 | Belleau et al. |
| 5,047,407 A | 9/1991 | Belleau et al. |
| 5,059,690 A | 10/1991 | Zahler et al. |
| 5,185,437 A | 2/1993 | Koszalka et al. |
| 5,270,315 A | 12/1993 | Belleau et al. |
| 5,770,713 A | 6/1998 | Imbach ...................... 536/22.1 |
| 5,770,725 A | 6/1998 | Gosselin et al. ........... 536/26.8 |
| 5,849,905 A | 12/1998 | Gosselin et al. ......... 536/25.33 |

FOREIGN PATENT DOCUMENTS

| | | |
|---|---|---|
| EP | 0 217 580 | 4/1987 |
| EP | 0337713 | 4/1989 |
| EP | 0375329 | 6/1990 |
| EP | 0433898 | 12/1990 |
| EP | 0515157 | 5/1992 |
| EP | 0494119 | 7/1992 |
| EP | 0515144 | 11/1992 |
| EP | 0515156 | 11/1992 |
| EP | 0526253 | 2/1993 |
| WO | WO 88/07532 | 10/1988 |
| WO | WO 91/11186 | 8/1991 |
| WO | WO 92/00315 | 1/1992 |
| WO | WO 92/10496 | 6/1992 |
| WO | WO 92/10497 | 6/1992 |
| WO | WO 92/14743 | 9/1992 |
| WO | WO 92/15308 | 9/1992 |
| WO | WO 92/18517 | 10/1992 |
| WO | WO 93/12128 | 6/1993 |
| WO | WO 93/12131 | 6/1993 |
| WO | WO 93/12132 | 6/1993 |
| WO | WO 93/24510 | 12/1993 |
| WO | WO 94/05300 | 3/1994 |
| WO | WO 94/14456 | 7/1994 |
| WO | WO 94/14802 | 7/1994 |
| WO | WO 94/26764 | 11/1994 |
| WO | WO 95/11252 | 4/1995 |
| WO | WO 96/40164 | 12/1996 |

OTHER PUBLICATIONS

Schinazi, R.F., et al., "Pure Nucleoside Enantiomers of β–2'–3'–Dideoxycytidine Analogs are Selective Inhibitors of Hepatitis B Virus in Vitro," *Antimicrobial Agents and Chemotherapy*, vol. 38, No. 9, Sep. 1994, p. 2172–2174.

U.S. patent application Ser. No. 07/686,617, Cheng, filed Apr. 17, 1991.

U.S. patent application Ser. No. 07/718,806, Cheng, filed Jun. 21, 1991.

U.S. patent application Ser. No. 07/785,545, Cheng, filed Oct. 31, 1991.

Balzarini, J., et al., "Potent and Selective Anti–HTLV–III/LAV Activity of 2',3'–Dideoxycytidinene, the 2',3'–Unsaturated Derivative of 2',3'–Dideoxycytidine," *Biochemical and Biophysical Research Communications*, vol. 140, No. 2, pp. 735–742 (1986).

Carter, et al., "Activites of (–)–Carbovir and 3'–Azido–3'–Deoxythymidine Against Human Immunodeficiency Virus In Vitro," *Antimicrobial Agents and Chemotherapy*, vol. 34, No. 6, pp. 1297–1300 (1990).

Chu, et al., "Structure–Activity Relationships of Pyrimidine Nucleosides as Antiviral Agents for Human Immunodeficiency Virus Type 1 in Peripheral Blood Mononuclear Cells," *J. Med. Chem.* vol. 32, p. 612 (1989).

Chu, et al., "Comparative Activity of 2',3'–Saturated and Unsaturated Pyrimidine and Purine Nucleosides Against Human Immunodeficiency Virus Type 1 in peripheral Blood Mononuclear Cells," *Biochem. Pharm.*, vol. 37, No. 19, pp. 3543–3548 (1988).

Chu, C.K., et al., "An Efficient Total Synthesis fo 3'–Azido–3'–Deoxythiymidine (AZT) and 3'–Azido–2', 3'–Dideoxyuridine (AZDDU, CS–87) from D–Mannitol," *Tetrahedron Lett.* 1988, 5349.

(List continued on next page.)

*Primary Examiner*—Samuel Barts
*Assistant Examiner*—Howard V. Owens, Jr.
(74) *Attorney, Agent, or Firm*—Sherry M. Knowles; King & Spalding

(57) ABSTRACT

A method for treating HBV infections via administration of 2', 3' dideoxynucleoside compounds.

11 Claims, 2 Drawing Sheets

OTHER PUBLICATIONS

Cretton, E., et al., "Pharmokinetics of 3'-Azido-3'-Dexoythymidine and its Catabolites and Interactions with Probenecid in Rhesus Monkeys," *Antimicrobial Agents and Chemotherapy*, pp. 801–807 (1991).

Cretton, E., et al., "Catabolism of 3'-Azido-3'-Deoxythymidine in Heptaocytes and Liver Microsomes, with Evidence of Formation of 3'-Amino-3'-Deoxythymidine, a Highly Toxic Catabolite for Human Bone Marrow Cells," *Pharmacology*, vol. 39, p. 258.

Jeong, I., et al., "Asymmetric Synthesis and Biological Evaluation of β–L–(2R,5S)– and α–L–(2R–5R)–1,3–Oxathiolane–Pyrimidine and –Purine Nucleosides and Potential Anti–HIV Agents," *J. Med. Chem.*, vol. 36 (1993).

Krenitsky, T.A., et al., "3'-Amino-2',3'-Dideoxyridonucleosides of Some Pyrimidines: Synthesis and Biological Activities," *J. Med. Chem*, Vo. 26 (1983).

Lin, et al., "Potent and Selective In Vitro Activity of 3'-Deoxythmindine-2-Ene-(3'-Deoxy-2',3'-Didehydrothymidine) Against Human Immunodeficiency Virus," *Biochem. Pharm.*, vol. 36, No. 17, p. 2716 (1987).

Mitsuya, H., et al., "Rapid in Vitro Systems for Assessing Activity of Agents Against HTLV–III/LAV," *AIDS: Modern Concepts and Therapeutic Challenges,* S. Broder, Ed. (Marcel–Dekker, New York, 1987), pp. 303.

Mitsuya, J., et al., 3'-Azido-3'-Deoxythymidine (BW A 509U); An Antiviral Agent that Inhibits the Infectivity and Cytopathic Effect of Human T–Lymphotropic Virus Type III/Lymphadenopathy–Associated Virus In Vitro, *Proc. Natl. Acad. Sci., USA* vol. 82, pp. 7097–7100 (1985).

Norbeck, D., et al., "A New 2',3'–Dideoxynucleoside Prototype with In Vitro Activity Against HIV," *Tetrahedron Lett.* 1989, 6263.

Okabe, M., et al., "Synthesis of the Dideoxynucleosides ddC and CNT from Glutamic Acid. Ribonolactone, and Pyrimidine Bases," *J. Org. Chem.* 1989.

Richman, D. D., et al., "The Toxicity of Azidothymidine (AZT) in the Treatment of Patients with AIDS–Related Complex," *N. Eng. J. Med.* 1987, 317:192.

Satsumabayashi, S. et al., "the Synthesis of 1,3–Oxathiolane–5–one Derivatives," *Bull. Chem. Soc. Japan,* 1972, 45,913.

Schinazi, R.F., et al., "Insights into HIV Chemotherapy," *AIDS Research and Human Retroviruses* 8(6) (1992) 963–990.

Schinazi, R.F., et al., "Substrate Specificity of *Escherichia Coli* Thymidine Phosphorylase for Pyrimidine Nucleoside with an Anti–Human Immunodeficiency Virus Activity," *Biochemical Pharmacology* 44(2) (1992) 199–204.

Sterzycki, R.Z., et al., "Synthesis and anti–HIV activity of several 2'–fluoro–containing pyrimidine nucleosides," *J. Med. Chem.* 33:2150–2157 (1990).

Vorbrüggen et al., "Nucleoside Synthesis with Trimethylsilyl Triflate and Perchlorate as Catalysts," *Chem. Ber.* 1981, 114:1234–1255.

Wilson, L.J., et al., "A General Method for Controlling Glycosylation Stereochemistry in the Synthesis of 2'–Deoxyribose Nucleosides," *Tetrahedron Lett.* 1990, 1815.

Jurovcik, M. et al., "Metabolism of pyrimidine L–nucleosides." Nucleic Acids Res. vol. 3, No. 8, Aug. 1976, p. 2143–54.

Piantadosi C. et al., "Synthesis and evaluation of novel ether lipid nucleoside conjugates for anti–HIV–1 activity," J. Med. Chem. vol. 34, No. 4:1408–14. Apr. 1991, p. 1408–1414.

NUCLEOSIDES WITH ANTI-HEPATITIS B VIRUS ACTIVITY

This application is a continuation of U.S. Ser. No. 08/829,748 filed on Mar. 31, 1997 now U.S. Pat. No. 5,990,093, by Raymond F. Schinazi, Jean-Pierre Sommadossi, Giles Gosselin and Jean-Louis Imbach for "Nucleosides with Anti-Hepatitis B Activity," which is a continuation of U.S. Ser. No. 08/587,598 filed on Dec. 22, 1995 (now abandoned), which is a continuation of U.S. Ser. No. 08/320,461 filed on Oct. 7, 1994 (now abandoned), which is a continuation of U.S. Ser. No. 08/119,470 filed on Sep. 10, 1993 (now abandoned).

BACKGROUND OF THE INVENTION

This invention is in the area of methods for the treatment of hepatitis B virus (also referred to as "HBV") that includes administering an effective amount of one or more of the active compounds disclosed herein, or a pharmaceutically acceptable derivative or prodrug of one of these compounds.

HBV is second only to tobacco as a cause of human cancer. The mechanism by which HBV induces cancer is unknown, although it is postulated that it may directly trigger tumor development, or indirectly trigger tumor development through chronic inflammation, cirrhosis, and cell regeneration associated with the infection.

Hepatitis B virus has reached epidemic levels worldwide. After a two to six month incubation period in which the host is unaware of the infection, HBV infection can lead to acute hepatitis and liver damage, that causes abdominal pain, jaundice, and elevated blood levels of certain enzymes. HBV can cause fulminant hepatitis, a rapidly progressive, often fatal form of the disease in which massive sections of the liver are destroyed. Patients typically recover from acute viral hepatitis. In some patients, however, high levels of viral antigen persist in the blood for an extended, or indefinite, period, causing a chronic infection. Chronic infections can lead to chronic persistent hepatitis. Patients infected with chronic persistent HBV are most common in developing countries. By mid-1991, there were approximately 225 million chronic carriers of HBV in Asia alone, and worldwide, almost 300 million carriers. Chronic persistent hepatitis can cause fatigue, cirrhosis of the liver, and hepatocellular carcinoma, a primary liver cancer.

In western industrialized countries, high risk groups for HBV infection include those in contact with HBV carriers or their blood samples. The epidemiology of HBV is in fact very similar to that of acquired immunodeficiency syndrome, which accounts for why HBV infection is common among patients with AIDS or HIV-associated infections. However, HBV is more contagious than HIV.

Daily treatments with α-interferon, a genetically engineered protein, has shown promise. A human serum-derived vaccine has also been developed to immunize patients against HBV. Vaccines have been produced through genetic engineering. While the vaccine has been found effective, production of the vaccine is troublesome because the supply of human serum from chronic carriers is limited, and the purification procedure is long and expensive. Further, each batch of vaccine prepared from different serum must be tested in chimpanzees to ensure safety. In addition, the vaccine does not help the patients already infected with the virus.

European Patent Application No. 92304530.6 discloses that a group of 1,2-oxathiolane nucleosides are useful in the treatment of hepatitis B infections. It has been reported that the 2-hydroxymethyl-5-(cytosin-1-yl)-1,3-oxathiolane has anti-hepatitis B activity. Doong, et al., *Proc. of Natl. Acad. Sci, USA*, 88, 8495–8499 (1991); Chang, et al., *J. of Biological Chem.*, Vol 267(20), 13938–13942. The anti-hepatitis B activity of the (−) and (+)-enantiomers of 2-hydroxymethyl-5-(5-fluorocytosin-1-yl)-1,3-oxathiolane has been published by Furman, et al., in *Antimicrobial Agents and Chemotherapy*, Dec. 1992, pages 2686–2692.

In light of the fact that hepatitis B virus has reached epidemic levels worldwide, and has severe and often tragic effects on the infected patient, there remains a strong need to provide new effective pharmaceutical agents to treat humans infected with the virus that have low toxicity to the host.

Therefore, it is another object of the present invention to provide a method and composition for the treatment of human patients or other hosts infected with HBV.

SUMMARY OF THE INVENTION

A method for the treatment of a host, and in particular, a human, infected with HBV is provided that includes administering an HBV-treatment amount of a nucleoside of the formula:

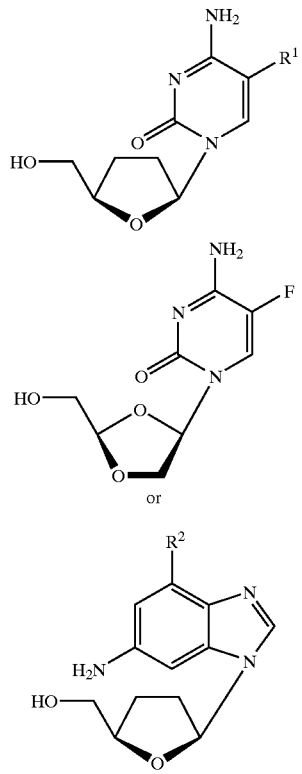

wherein: $R^1$ is hydrogen, fluoro, bromo, chloro, iodo, methyl or ethyl; and $R^2$ is OH, Cl, $NH_2$, or H; or a pharmaceutically acceptable salt of the compound, optionally in a pharmaceutically acceptable carrier or diluent. In a preferred embodiment, the nucleoside is provided as the indicated enantiomer and substantially in the absence of its corresponding enantiomer (i.e., in enantiomerically enriched form).

In an alternative embodiment, the β-L-enantiomer of a compound of the formula:

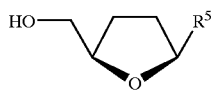

wherein $R^5$ is adenine, xanthine, hypoxanthine, or other purine, including an alkylated or halogenated purine is administered to a host in an HBV-treatment amount as described more fully herein.

In another embodiment, the invention includes a method for the treatment of humans infected with HBV that includes administering an HBV treatment amount of a prodrug of the specifically disclosed nucleosides. A prodrug, as used herein, refers to a pharmaceutically acceptable derivative of the specifically disclosed nucleoside, that is converted into the nucleoside on administration in vivo, or that has activity in itself. Nonlimiting examples are the 5' and $N^4$-pyrimidine or $N^6$-purine acylated or alkylated derivatives of the active compound.

The disclosed nucleosides, or their pharmaceutically acceptable prodrugs or salts or pharmaceutically acceptable formulations containing these compounds are useful in the prevention and treatment of HBV infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. These compounds or formulations can also be used prophylactically to prevent or retard the progression of clinical illness in individuals who are anti-HBV antibody or HBV-antigen positive or who have been exposed to HBV.

In one embodiment of the invention, one or more of the active compounds is administered in alternation or combination with one or more other anti-HBV agents, to provide effective anti-HBV treatment. Examples of anti-HBV agents that can be used in alternation or combination therapy include but are not limited to the (−)-enantiomer or racemic mixture of 2-hydroxymethyl-5-(5-fluorocytosin-1-yl)-1,3-oxathiolane ("FTC", see WO 92/14743), its physiologically acceptable derivative, or physiologically acceptable salt; the (−)-enantiomer or racemic mixture of 2-hydroxymethyl-5-(cytosin-1-yl)-1,3-oxathiolane (also referred to as "BCH-189" or 3TC, see EPA Publication No. 0 382 526), its physiologically acceptable derivative, or physiologically acceptable salt; an enantiomer or racemic mixture of 2'-fluoro-5-iodo-arabinosyluracil (FIAU); an enantiomer or racemic mixture of 2'-fluoro-5-ethyl-arabinosyluracil (FEAU); carbovir, or interferon.

Any method of alternation can be used that provides treatment to the patient. Nonlimiting examples of alternation patterns include 1–6 weeks of administration of an effective amount of one agent followed by 1–6 weeks of administration of an effective amount of a second anti-HBV agent. The alternation schedule can include periods of no treatment. Combination therapy generally includes the simultaneous administration of an effective ratio of dosages of two or more anti-HBV agents.

In light of the fact that HBV is often found in patients who are also anti-HIV antibody or HIV-antigen positive or who have been exposed to HIV, the active anti-HBV compounds disclosed herein or their derivatives or prodrugs can be administered in the appropriate circumstance in combination or alternation with anti-HIV medications, including but not limited to 3'-azido-3'-deoxythymidine (AZT), 2',3'-dideoxyinosine (DDI), 2',3'-dideoxycytidine (DDC), 2',3'-dideoxy-2', 3'-didehydrothymidine (D4T), 2-hydroxymethyl-5-(5-fluorocytosin-1-yl)-1,3-oxathiolane (FTC), or 2-hydroxymethyl-5-(cytosin-1-yl)-1,3-oxathiolane (BCH-189), in racemic or enantiomeric form. Non-nucleoside RT-inhibitors such as the Tibo class of compounds, nevirapine, or pyrimidinone can also be administered in combination with the claimed compounds.

The active anti-HBV agents can also be administered in combination with antibiotics, other antiviral compounds, antifungal agents, or other pharmaceutical agents administered for the treatment of secondary infections.

DETAILED DESCRIPTION OF THE INVENTION

As used, herein, the term "enantiomerically pure" refers to a nucleoside composition that includes at least approximately 95%, and preferably approximately 97%, 98%, 99%, or 100% of a single enantiomer of that nucleoside.

As used herein, the term alkyl specifically includes but is not limited to $C_1$ to $C_{10}$ methyl, ethyl, propyl, butyl, pentyl, hexyl, isopropyl, isobutyl, sec-butyl, t-butyl, isopentyl, amyl, t-pentyl, cyclopentyl, and cyclohexyl.

As used herein, the term acyl specifically includes but is not limited to acetyl, propionyl, butyryl, pentanoyl, 3-methylbutyryl, hydrogen succinate, 3-chlorobenzoate, benzoyl, acetyl, pivaloyl, mesylate, propionyl, valeryl, caproic, caprylic, capric, lauric, myristic, palmitic, stearic, and oleic.

As used herein, the term natural amino acid includes but is not limited to alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl.

As used herein, and unless otherwise defined, the term aryl refers to phenyl.

The invention as disclosed herein is a method and composition for the treatment of HBV infection and other viruses replicating in a like manner, in humans or other host animals, that includes administering an effective amount of one or more of the above-identified compounds, or a physiologically acceptable derivative, or a physiologically acceptable salt thereof, optionally in a pharmaceutically acceptable carrier. The compounds of this invention either possess anti-HBV activity, or are metabolized to a compound or compounds that exhibit anti-HBV activity.

I. Structure and Preparation of Active Nucleosides
Stereochemistry

The compounds used in the methods disclosed herein are enantiomers of 2',3'-dideoxycytidine, 2',3'-dideoxy-5-(halo or methyl)cytidine, 2-hydroxymethyl-5-(5-fluorocytosin-1-yl)-1,3-dioxolane, or 2-amino-6-(OH, Cl, $NH_2$, or H)-9-[(4-hydroxymethyl)-tetrahydrofuran-1-yl]purine.

Figure 1:
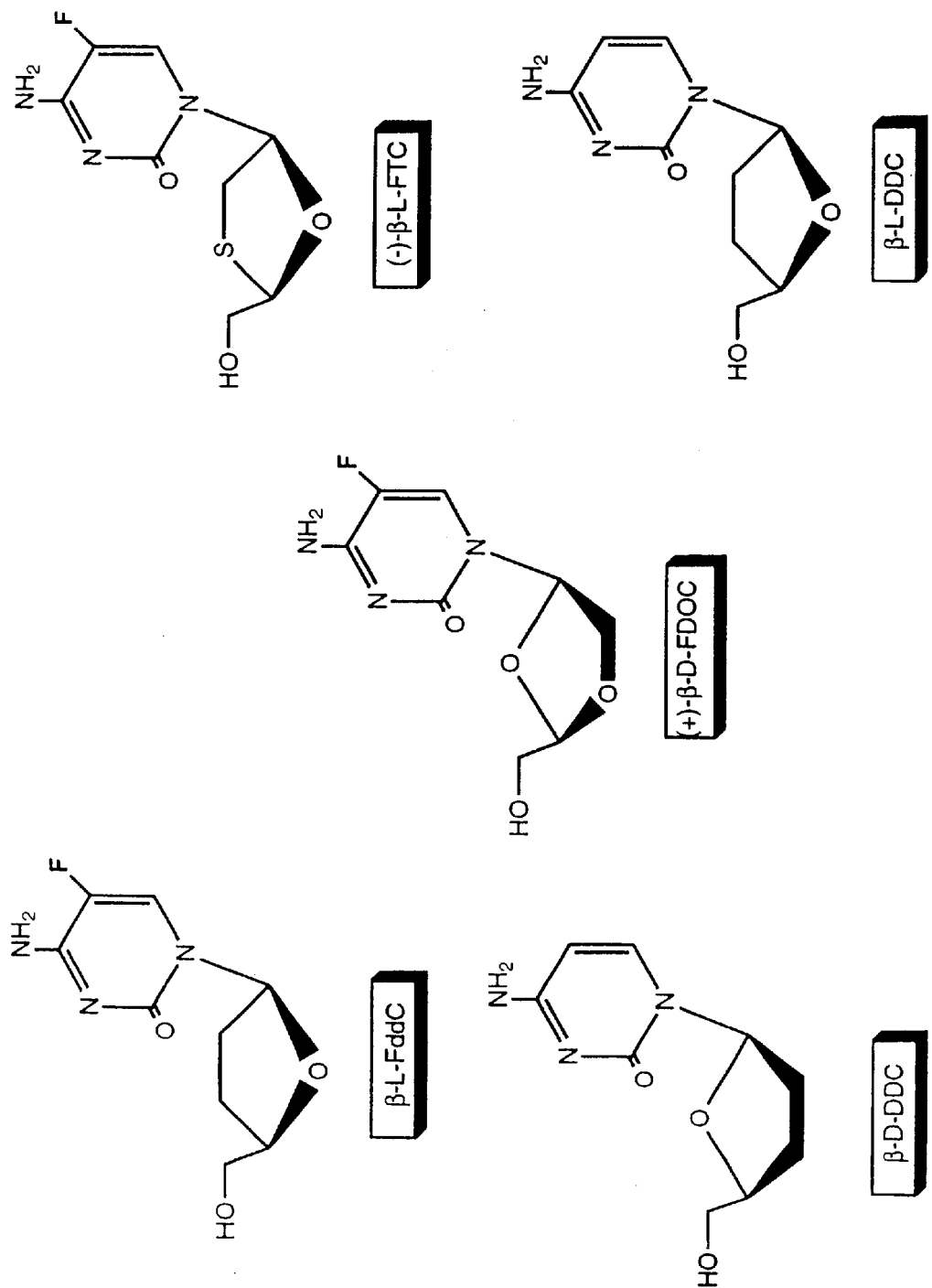
FIG. 1 is an illustration of the chemical structures of β-L-2',3'-dideoxycytidine (β-L-FddC), β-D-2',3'-dideoxycytidine (β-D-ddC), β-L-2',3'-dideoxy-5-fluorocytidine (β-L-ddC), (−)-β-L-2-hydroxymethyl-5-(5-fluorocytosin-1-yl)-1,3-oxathiolane ((−)-β-L-FTC), (+)-β-D-2-hydroxymethyl-5-(5-fluorocytosin-1-yl)-1,3-dioxolane ((+)-β-D-FDOC), and β-L-2-amino-6-($R^4$) -9-[(4-hydroxymethyl) -tetrahydrofuran-1-yl]purine.
Figure 2:
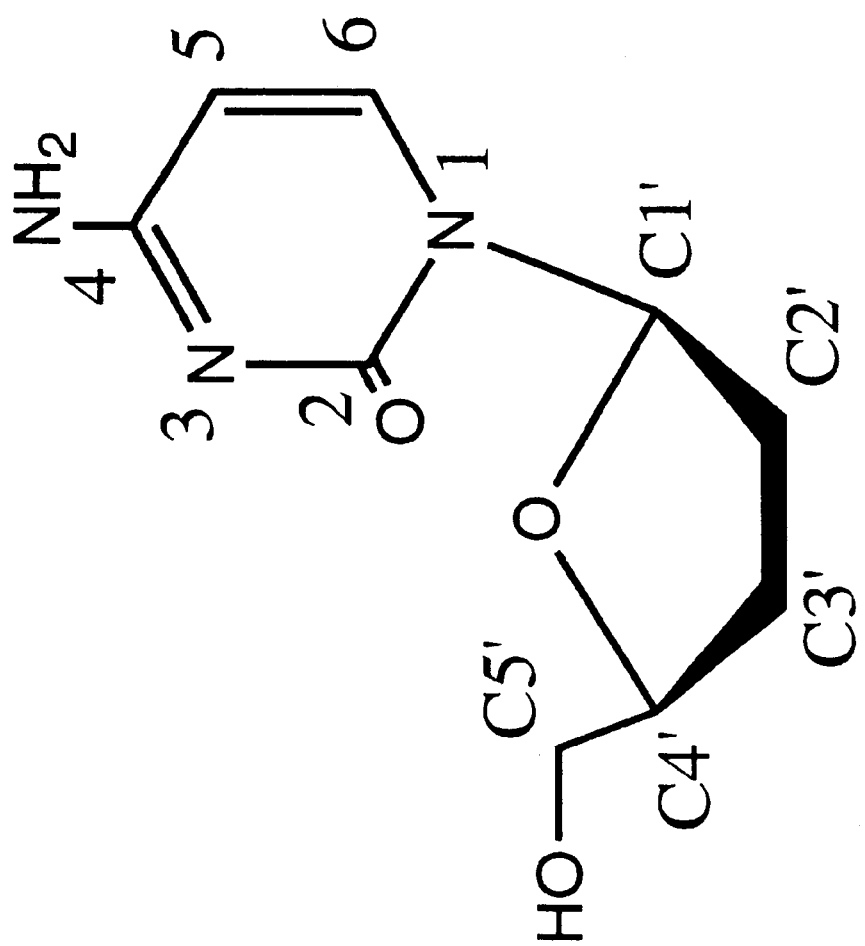
FIG. 2 is an illustration of the numbering scheme used in the chemical nomenclature for nucleosides in this text.

Since the 1' and 4' carbons of the sugar or dioxolanyl moiety (referred to below generically as the sugar moiety) of the nucleosides are chiral, their nonhydrogen substituents ($CH_2OR$ and the pyrimidine or purine base, respectively) can be either cis (on the same side) or trans (on opposite sides) with respect to the sugar ring system. The four optical isomers therefore are represented by the following configurations (when orienting the sugar moiety in a horizontal plane such that the "primary" oxygen (that between the C1' and C4'-atoms; see FIG. 2) is in back): cis (with both groups "up", which corresponds to the configuration of naturally occurring nucleosides), cis (with both groups "down", which is a nonnaturally occurring configuration), trans (with the C2 substituent "up" and the C5 substituent "down"), and trans (with the C2 substituent "down" and the C5 substituent "up"). As indicated schematically in FIG. 1, the "D-nucleosides" are cis nucleosides in a natural configuration and the "L-nucleosides" are cis nucleosides in the nonnaturally occurring configuration.

The nucleosides useful in the disclosed method to treat HBV infection are β-L-enantiomers, with the exception of FDOC, which is used in its β-D-enantiomeric form, because it has been discovered that the β-D-enantiomer of FDOC is surprisingly less toxic than the β-L-enantiomer of FDOC.

Prodrug Formulations

The nucleosides disclosed herein can be administered as any derivative that upon administration to the recipient, is capable of providing directly or indirectly, the parent active compound, or that exhibits activity in itself. Nonlimiting examples of prodrug embodiments of the active compounds include, but are not limited to those of the structure:

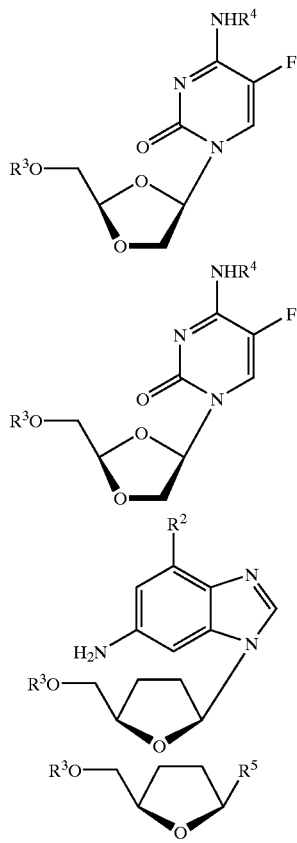

wherein:

$R^1$ is hydrogen, fluoro, bromo, chloro, iodo, methyl, or ethyl;

$R^2$ is OH, Cl, $NH_2$, or H;

$R^3$ is hydrogen; $C_1$–$C_{20}$ alkyl; acyl in which the non-carbonyl moiety of the ester group is selected from straight, branched, or cyclic $C_1$–$C_{20}$ alkyl, phenyl, or benzyl; a naturally occurring or nonnaturally occurring amino acid; alkoxyalkyl including methoxymethyl; aralkyl including benzyl; aryloxyalkyl such as phenoxymethyl; aryl including phenyl optionally substituted with halogen, $C_1$ to $C_4$ alkyl or $C_1$ to $C_4$ alkoxy; a dicarboxylic acid such as succinic acid; sulfonate esters such as alkyl or aralkyl sulphonyl including methanesulfonyl; or a mono, di or triphosphate ester; and $R^4$ is hydrogen; $C_1$–$C_{20}$ alkyl; acyl in which the non-carbonyl moiety of the ester group is selected from straight, branched, or cyclic $C_1$–$C_{20}$ alkyl, phenyl, or benzyl; alkoxyalkyl including methoxymethyl; aralkyl including benzyl; aryloxyalkyl such as phenoxymethyl; aryl including phenyl optionally substituted with halogen, $C_1$ to $C_4$ alkyl or $C_1$ to $C_4$ alkoxy.

The active nucleoside can also be provided as a 5'-ether lipid, as disclosed in the following references, which are incorporated by reference herein: Kucera, L. S., N. Iyer, E. Leake, A. Raben, Modest E. J., D. L. W., and C. Piantadosi. 1990. Novel membrane-interactive ether lipid analogs that inhibit infectious HIV-1 production and induce defective virus formation. AIDS Res Hum Retroviruses. 6:491–501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. Synthesis and evaluation of novel ether lipid nucleoside conjugates for anti-HIV activity. J Med Chem. 34:1408.1414; Hostetler, K. Y., D. D. Richman, D. A. Carson, L. M. Stuhmiller, G. M. T. van Wijk, and H. van den Bosch. 1992. Greatly enhanced inhibition of human immunodeficiency virus type 1 replication in CEM and HT4-6C cells by 3'-deoxythymidine diphosphate dimyristoylglycerol, a lipid prodrug of 3'-deoxythymidine. Antimicrob Agents Chemother. 36:2025.2029; Hostetler, K. Y., L. M. Stuhmiller, H. B. Lenting, H. van den Bosch, and D. D. Richman. 1990. Synthesis and antiretroviral activity of phospholipid analogs of azidothymidine and other antiviral nucleosides. *J. Biol Chem*. 265:6112.7.

Preparation of the Active Compounds

The nucleosides used in the disclosed method to treat HBV infections in a host organism can be prepared according to published methods. β-L-Nucleosides can be prepared from methods disclosed in, or standard modifications of methods disclosed in, for example, the following publications: Jeong, et al., J. of Med. Chem., 36, 182–195, 1993; European Patent Application Publication No. 0 285 884; Genu-Dellac, C., G. Gosselin, A.-M. Aubertin, G. Obert, A. Kirn, and J.-L. Imbach, 3-Substituted thymine α-L-nucleoside derivatives as potential antiviral agents; synthesis and biological evaluation, *Antiviral Chem. Chemother*. 2:83–92 (1991); Johansson, K. N. G., B. G. Lindborg, and R. Noreen, European Patent Application 352 248; Mansuri, M. M., V. Farina, J. E. Starrett, D. A. Benigni, V. Brankovan, and J. C. Martin, Preparation of the geometric isomers of DDC, DDA, D4C and D4T as potential anti-HIV agents, *Bioorg. Med. Chem. Lett*. 1:65–68 (1991); Fujimori, S., N. Iwanami, Y. Hashimoto, and K. Shudo, A convenient and stereoselective synthesis of 2'-deoxy-β-L-ribonucleosides, *Nucleosides & Nucleotides* 11:341–349 (1992); Genu-Dellac, C., G. Gosselin, A.-M. Aubertin, G. Obert, A. Kirn, and J.-L. Imbach, 3-Substituted thymine α-L-nucleoside derivatives as potential antiviral agents; synthesis and biological evaluation, *Antiviral Chem. Chemother*. 2:83–92

(1991); Holy, A, Synthesis of 2'-deoxy-L-uridine, *Tetrahedron Lett.* 2:189–192 (1992); Holy, A., Nucleic acid components and their analogs. CLIII. Preparation of 2'-deoxy-L-ribonucleosides of the pyrimidine series. *Collect Czech Chem Commun.* 37:4072–4087 (1992); Holy, A, 2'-deoxy-L-uridine: Total synthesis of a uracil 2'-deoxynucleoside from a sugar 2-aminooxazoline through a 2.2'-anhydronucleoside intermediate. In: Townsend LB, Tipson RS, ed. Nucleic Acid Chem. New York: Wiley, 1992: 347–353. Vol 1) (1992); Okabe, M., R.-C. Sun, S. Tan, L. Todaro, and D. L. Coffen, Synthesis of the dideoxynucleosides ddC and CNT from glutamic acid, ribonolactone, and pyrimidine bases. *J. Org. Chem.* 53:4780–4786 (1988); Robins, M. J., T. A. Khwja, and R. K. Robins. Purine nucleosides. XXIX. Synthesis of 21-deoxy-L-adenosine and 21-deoxy-L-guanosine and their alpha anomers. *J Org Chem.* 35:363–639 (1992); Genu-Dellac, C., Gosselin G., Aubertin A-M, Obert G., Kirn A., and Imbach J-L, 3'-Substituted thymine α-L-nucleoside derivatives as potential antiviral agents; synthesis and biological evaluation. *Antiviral Chem. Chemother.* 2(2):83–92 (1991); Génu-Dellac, C., Gosselin G., Imbach J-L; Synthesis of new 2'-deoxy-3'-substituted-α-L-threo-pentofuranonucleosides of thymine as a potential antiviral agents. *Tet Lett* 32(1):79–82 (1991); Génu-Dellac, C., Gosselin G., Imbach J-L, Preparation of new acylated derivatives of L-arabinofuranose and 2-deoxy-1-erythro-pentofuranose as precursors for the synthesis of 1-pentofuranosyl nucleosides. 216:240–255 (1991); and Génu-Dellac, C., Gosselin G., Puech F, et al. Systematic synthesis and antiviral evaluation of α-L-arabinofuranosyl and 2'-deoxy-α-L-erythro-pento-furanosyl nucleosides of the five naturally occurring nuclei acid bases. 10(b):1345–1376 (1991).

2',3'-Dideoxycytidine (DDC) is a known compound. The D-enantiomer of DDC is currently being marketed by Hoffman-LaRoche under the name Zalcitabine for use in the treatment of persons infected with HIV. See U.S. Pat. Nos. 4,879,277 and 4,900,828.

Enantiomerically pure β-D-dioxolane-nucleosides such as β-D-FDOC can be prepared as disclosed in detail in PCT/US91/09124. The process involves the initial preparation of (2R,4R)- and (2R,4S)-4-acetoxy-2-(protected-oxymethyl)-dioxolane from 1,6-anhydromannose, a sugar that contains all of the necessary stereochemistry for the enantiomerically pure final product, including the correct diastereomeric configuration about the 1 position of the sugar (that becomes the 4'-position in the later formed nucleoside). The (2R,4R)- and (2R,4S)-4-acetoxy-2-(protected-oxymethyl)-dioxolane is condensed with a desired heterocyclic base in the presence of $SnCl_4$, other Lewis acid, or trimethylsilyl triflate in an organic solvent such as dichloroethane, acetonitrile, or methylene chloride, to provide the stereochemically pure dioxolane-nucleoside.

Enzymatic methods for the separation of D and L enantiomers of cis-nucleosides are disclosed in, for example, Nucleosides and Nucleotides, 12(2), 225–236 (1993); European Patent Application Nos. 92304551.2 and 92304552.0 filed by Biochem Pharma, Inc.; and PCT Publication Nos. WO 91/11186, WO 92/14729, and WO 92/14743 filed by Emory University.

Separation of the acylated or alkylated racemic mixture of D and L enantiomers of cis-nucleosides can be accomplished by high performance liquid chromatography with chiral stationary phases, as disclosed in PCT Publication No. WO 92/14729.

Mono, di, and triphosphate derivative of the active nucleosides can be prepared as described according to published methods. The monophosphate can be prepared according to the procedure of Imai et al., *J. Org. Chem.*, 34(6), 1547–1550 (June 1969). The diphosphate can be prepared according to the procedure of Davisson et al., *J. Org. Chem.*, 52(9), 1794–1801 (1987). The triphosphate can be prepared according to the procedure of Hoard et al., *J. Am. Chem. Soc.*, 87(8), 1785–1788 (1965).

II. Anti-HBV Activity of Dioxolane Nucleosides

The ability of the active compounds to inhibit HBV can be measured by various experimental techniques. The assay used herein to evaluate the ability of the disclosed compounds to inhibit the replication of HBV is described in detail in Korba and Gerin, Antiviral Res. 19: 55–70 (1992). For purposes of illustration only, and without limiting the invention, the results of the evaluation of toxicity and anti-HBV activity are provided below for β-L-2',3'-dideoxycytidine (β-L-FddC), β-L-2',3'-dideoxy-5-fluorocytidine (β-L-ddC), and (+)-β-D-2-hydroxymethyl-5-(5-fluorocytosin-1-yl)-1,3-dioxolane ((+)-β-D-FDOC). The toxicity and anti-HBV activity of (−)-β-L-2-hydroxymethyl-5-(5-fluorocytosin-1-yl)-1,3-oxathiolane ((−)-β-L-FTC) and β-D-2',3'-dideoxycytidine (β-D-ddC) are included as controls. The other compounds disclosed herein can be evaluated similarly.

The samples of β-L-ddC and β-L-5-FddC used in the anti-HBV assays were characterized as follows.

2',3'-Dideoxy-β-L-cytidine (β-L-DDC). m.p.=220–220° C.; UV (EtOH 95) max 273 nm, λmin 252 nm; NMR-$^1$H (DMSO-$d_6$) δppm=7.89 (d. 1H. H-6; J=7.4 Hz). 7.15–6.95 (d large, 2H, $NH_2$), 5.91 (dd. 1H, H-1'; J=3.0 et 6.5 Hz), 5.66 (d, 1H, H-5; J=7.4 Hz), 4.99 [t. 1H, OH-5'; J–5.2 Hz]. 4.05–3.95 (m, 1H, H-4'), 3.60–3.70 (m, 1H, H-5'; after $D_2O$ exchange: dd, 3.64 ppm, J=3.6 et 12.0 Hz). 3.60–3.50 (m. 1H, H-5"; after $D_2O$ exchange: dd, 3.50 ppm, J=4,1 et 12.0 Hz), 2.30–2.15 (m. 1H, H-2'), 1.9–1.65 (m. 3H, H-2", 3' et 3"); $[\alpha]_D^{20}$–103.6 (c 0.8 MeOH); mass spectrum (performed in: glycerol-thioglycerol, 50:50. v/v); FAB>0 423 [2M+H]$^+$, 304 [M+glycerol+H]$^+$. 212 [M+H]$^+$, 112 [$BH_2$]$^+$, 101 [s]$^+$; FAB<O 210 [M-H]$^-$. Anal. Calc. for $C_9H_{13}N_3O_3$ (M=211.21); C 51.18; H 6.20; N 19.89 found; C 51.34; H 6.25; N 20.12.

2',3'-Dideoxy-β-L-5-fluorocytidine (β-L-5-FDDC). m.p.= 158–160° C.; UV (EtOH 95) λmax 281 nm (ϵ, 8100) et 237 nm (ϵ, 8500); min 260 nm (ϵ, 5700) et 225 nm (ϵ, 7800); NMR—$^1$H (DMSO-$d_6$) δppm 8.28 (d. 1H, H-6; J=7.4 Hz), 7.7–7.4 (d large, 2H, $NH_2$), 5.83 (dd poorly resolved, 1H, H-1'), 5.16(t. 1H, OH-5'; J=5.1 Hz), 4.05–3.95 (m, 1H, H-4'), 3.8–3.70 [m, 1H, H 5'; after D20 exchange: dd, 3.71 ppm. J=2.7 et 12.3 Hz], 3.60–3.50 [m. 1H, H-5"; after $D_2O$ exchange: dd, 3.52 ppm; J=3.3 et 12.3 Hz], 2.35–2.15 (m, 1H, H-2'). 1.95–1.75 (m, 3H, H-2", 3' et 3"): $[\alpha]_D^{20}$–80.0 (-c 1.0, DMSO); Mass spectrum [performed in: 3-nitrobenzyl alcohol] FAB>0 230 [M+H]$^+$et 101 [s]$^+$; FAB<O 228 [M-II]$^-$. Anal. Calculated for $C_9H_{12}N_3OF_3$(M=229.21); C 47.16; II 5.28; N 18.33, F 8.29, Found. C 16.90; H 5.28; N 18.07; F 8.17.

The antiviral evaluations were performed on two separate passages of cells, two cultures per passage (4 cultures total). All wells, in all plates, were seeded at the same density and at the same time.

Due to the inherent variations in the levels of both intracellular and extracellular HBV DNA, only depressions greater than 3.0-fold (for HBV virion DNA) or 2.5-fold (for HBV DNA replication intermediates) from the average levels for these HBV DNA forms in untreated cells are generally considered to be statistically significant [P<0.05] (Korba and Gerin, Antiviral Res. 19: 55–70, 1992). The levels of integrated HBV DNA in each cellular DNA preparation (which remain constant on a per cell basis in these experiments) were used to calculate the levels of intracellular HBV DNA forms, thereby eliminating technical variations inherent in the blot hybridization assays.

Typical values for extracellular HBV virion DNA in untreated cells range from 50 to 150 pg/ml-culture medium (average of approximately 76 pg/ml). Intracellular HBV DNA replication intermediates in untreated cells range from 50 to 100 pg/ug cell DNA (average approximately 74 pg/ug cell DNA). In general, depressions in the levels of intracellular HBV DNA due to treatment with antiviral compounds are less pronounced, and occur more slowly, than depressions in the levels of HBV virion DNA.

For reference, the manner in which the hybridization analyses were performed for these experiments results in an equivalence of approximately 1.0 pg intracellular HBV DNA/ug cellular DNA to 2–3 genomic copies per cell and 1.0 pg of extracellular HBV DNA/ml culture medium to $3 \times 10^5$ viral particles/ml.

Toxicity analyses were performed in order to assess whether any observed antiviral effects were due to a general effect on cell viability. The method used was based on the uptake of neutral red dye, a standard and widely used assay for. cell viability in a variety of virus-host systems, including HSV (herpes simplex virus) and HIV.

The test compounds were used in the form of 40 mM stock solutions in DMSO (frozen on dry ice). Daily aliquots of the test samples were made and frozen at −20° C. so that each individual aliquot would be subjected to a single freeze-thaw cycle. The daily test aliquots were thawed, suspended into culture medium at room temperature and immediately added to the cell cultures. The compounds were tested at 0.01 to 10 $\mu$M for antiviral activity. The compounds were tested for toxicity at concentrations from 1 to 300 $\mu$M. The results are provided in Table 1.

The compounds were moderately toxic at 300 $\mu$M, however, all three compounds exhibited less toxicity at this concentration than β-D-ddC. It appears that the $IC_{50}$ of β-L-ddC and β-L-FddC is approximately twice that of β-D-ddC.

Toxicity analyses were performed in 96-well flat bottomed tissue culture plates. Cells for the toxicity analyses were cultured and treated with test compounds with the same schedule as used for the antiviral evaluations. Each compound was tested at 4 concentrations, each in triplicate cultures. Uptake of neutral red dye was used to determine the relative level of toxicity. The absorbance of internalized dye at 510 nM ($A_{510}$) was used for the quantitative analysis. Values are presented as a percentage of the average $A_{510}$ values (±standard deviations) in 9 separate cultures of untreated cells maintained on the same 96-well plate as the test compounds. The percentage of dye uptake in the 9 control cultures on plate 40 was 100±3. At 150–190 $\mu$M β-D-ddC, a 2-fold reduction in dye uptake (versus the levels observed in untreated cultures) is typically observed in these assays (Korba and Gerin, Antiviral Res. 19: 55–70, 1992).

EXAMPLE 3

Anti-Hepatitis B Virus Activity

The positive treatment control, β-D-2′,3′-dideoxycytosine [β-D-ddC], induced significant depressions of HBV DNA replication at the concentration used. Previous studies have indicated that at 9–12 $\mu$M of β-D-ddc, a 90% depression of HBV RI (relative to average levels in untreated cells) is typically observed in this assay system (Korba and Gerin, Antiviral Res. 19: 55–70, 1992). This is consistent with the data presented in Table 1.

The data presented in Table 1 indicates that all three test compounds ((β-L-FddC), (β-L-ddC), and β-D-FDOC)), were potent inhibitors of HBV replication, causing depression of HBV is virion DNA and HBV RI to a degree comparable to, or greater than, that observed following treatment with β-D-ddC.

TABLE 1

EFFECT OF D-DDC, L-DDC, L-FDDC, FDOC and (−)-FTC AGAINST HEPATITIS B VIRUS IN TRANSFECTED HEPG-2 (2.2.15) CELLS

| Compound | HBV virion[a] | | HBV RI[b] | | Cytotoxicity | Selectivity Index $IC_{50}/EC_{90}$ | |
|---|---|---|---|---|---|---|---|
| | $EC_{50}$ ± SD | $EC_{90}$ ± SD | $EC_{50}$ ± SD | $EC_{90}$ ± SD | $IC_{50}$ ± SD | Virion | RI |
| β-D-DDC | 1.3 ± 0.2[c] | 2.1 ± 0.3 | 8.1 ± 1.7 | 12.0 ± 2.4 | 219 ± 28[c] | 104 | 18 |
| | 1.5 ± 0.7 | 9.4 ± 2.5 | 3.2 ± 0.6 | 11.0 ± 2.0 | 216 ± 22 | 23 | 20 |
| β-L-DDC | 0.033 ± 0.003 | 1.1 ± 0.2 | 0.107 ± 0.012 | 1.8 ± 0.2 | 493 ± 64 | 448 | 274 |
| β-L-FDDC | 0.12 ± 0.01 | 0.30 ± 0.03 | 2.8 ± 0.4 | 4.8 ± 0.6 | 438 ± 57 | 1,460 | 91 |
| (+)-β-D-FDOC | 0.020 ± 0.003 | 0.195 ± 0.027 | 0.062 ± 0.012 | 0.23 ± 0.02 | 251 ± 23 | 1,287 | 1,091 |
| (−)-β-L-FTC | 0.017 ± 0.005 | 0.15 ± 0.02 | 0.049 ± 0.008 | 0.18 ± 0.03 | 292 ± 13 | 1,947 | 1,622 |

[a]Extracellular DNA
[b]Replicative intermediates (Intracellular DNA)
[c]$\mu$M

EXAMPLE 2

Toxicity of Compounds

The ability of the active compounds to inhibit the growth of virus in 2.2.15 cell cultures (HepG2 cells transformed with hepatitis virion) was evaluated. As illustrated in Table 1, no significant toxicity (greater than 50% depression of the dye uptake levels observed in untreated cells) was observed for any of the test compounds at the concentrations 100 $\mu$M.

IV. Preparation of Pharmaceutical Compositions

The compounds disclosed herein and their pharmaceutically acceptable salts, prodrugs, and derivatives, are useful in the prevention and treatment of HBV infections and other related conditions such as anti-HBV antibody positive and HBV-positive conditions, chronic liver inflammation caused by HBV, cirrhosis, acute hepatitis, fulminant hepatitis, chronic persistent hepatitis, and fatigue. These compounds or formulations can also be used prophylactically to prevent or retard the progression of clinical illness in individuals who are anti-HBV antibody or HBV-antigen positive or who have been exposed to HBV.

Humans suffering from any of these conditions can be treated by administering to the patient an effective HBV-treatment amount of one or a mixture of the active compounds described herein or a pharmaceutically acceptable derivative or salt thereof, optionally in a pharmaceutically acceptable carrier or diluent. The active materials can be administered by any appropriate route, for example, orally, parenterally, intravenously, intradermally, subcutaneously, or topically, in liquid or solid form.

The active compound is included in the pharmaceutically acceptable carrier or diluent in an amount sufficient to deliver to a patient a therapeutically effective amount without causing serious toxic effects in the patient treated.

A preferred dose of the active compound for all of the above-mentioned conditions will be in the range from about 1 to 60 mg/kg, preferably 1 to 20 mg/kg, of body weight per day, more generally 0.1 to about 100 mg per kilogram body weight of the recipient per day. The effective dosage range of the pharmaceutically acceptable derivatives can be calculated based on the weight of the parent nucleoside to be delivered. If the derivative exhibits activity in itself, the effective dosage can be estimated as above using the weight of the derivative, or by other means known to those skilled in the art. In one embodiment, the active compound is administered as described in the product insert or Physician's Desk Reference for 3'-azido-3'-deoxythymidine (AZT), 2',3'-dideoxyinosine (DDI), 2',3'-dideoxycytidine (DDC), or 2',3'-dideoxy-2',3'-didehydrothymidine (D4T) for HIV indication.

The compound is conveniently administered in unit any suitable dosage form, including but not limited to one containing 7 to 3000 mg, preferably 70 to 1400 mg of active ingredient per unit dosage form. A oral dosage of 50–1000 mg is usually convenient.

Ideally the active ingredient should be administered to achieve peak plasma concentrations of the active compound of from about 0.2 to 70 $\mu$M, preferably about 1.0 to 10 $\mu$M. This may be achieved, for example, by the intravenous injection of a 0.1 to 5% solution of the active ingredient, optionally in saline, or administered as a bolus of the active ingredient.

The active compound can be provided in the form of pharmaceutically acceptable salts. As used herein, the term pharmaceutically acceptable salts or complexes refers to salts or complexes of the nucleosides that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with S cations such as sodium, potassium, zinc, calcium, bismuth, barium, magnesium, aluminum, copper, cobalt, nickel, cadmium, sodium, potassium, and the like, or with an organic cation formed from N,N-dibenzylethylene-diamine, ammonium, or ethylenediamine; or (c) combinations of (a) and (b); e.g., a zinc tannate salt or the like.

Modifications of the active compound, specifically at the $N^6$ or $N^4$ and 5'-O positions, can affect the bioavailability and rate of metabolism of the active species, thus providing control over the delivery of the active species.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound, or pharmaceutically acceptable derivative or salt thereof can also be mixed with other active materials that do not impair the desired action, or with materials that supplement the desired action, such as antibiotics, antifungals, antiinflammatories, or other antivirals, including anti-HBV, anti-cytomegalovirus, or anti-HIV agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS). In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

This invention has been described with reference to its preferred embodiments. Variations and modifications of the invention, will be obvious to those skilled in the art from the foregoing detailed description of the invention. It is intended that all of these variations and modifications be included within the scope of the appended claims.

We claim:

1. A method for the treatment of HBV infection in a human or other host animal, comprising administering an HBV treatment amount of a nucleoside of the structure:

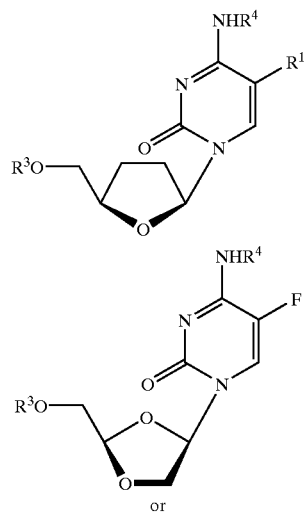

or

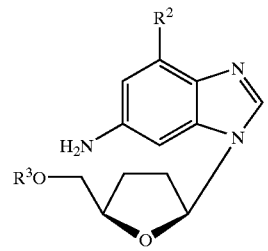

wherein: $R^1$ is hydrogen, fluoro, bromo, chloro, iodo or methyl;

$R^2$ is OH, Cl, $NH_2$, or H;

$R^3$ is hydrogen; $C_1$–$C_{20}$ alkyl; acyl in which the non-carbonyl moiety of the ester group is selected from straight, branched; or cyclic $C_1$–$C_{20}$ alkyl, phenyl, or benzyl; a naturally occurring or nonnaturally occurring amino acid; alkoxyalkyl including methoxymethyl; aralkyl including benzyl; aryloxyalkyl such as phenoxymethyl; aryl including phenyl optionally substituted with halogen, $C_1$ to $C_4$ alkyl or $C_1$ to $C_4$ alkoxy; a dicarboxylic acid such as succinic acid; sulfonate esters such as alkyl or aralkyl sulphonyl including methanesulfonyl; or a mono, di or triphosphate ester; and $R^4$ is hydrogen; $C_1$–$C_{20}$ alkyl;, acyl, in which the non-carbonyl moiety of the ester group is selected from straight, branched, or cyclic $C_1$–$C_{20}$ alkyl, phenyl; or benzyl; alkoxyalkyl including methoxymethyl; aralkyl including benzyl; aryloxyalkyl such as phenoxymethyl; aryl including phenyl optionally substituted with halogen, $C_1$ to $C_4$ alkyl or $C_1$ to $C_4$ alkoxy; and wherein the compound is 95% free of its opposite β-(D or L) enantiomer.

2. The method of claim 1 wherein the carrier is suitable for oral delivery.

3. The method of claim 1 wherein the carrier comprises a capsule.

4. The method of claim 1 wherein the carrier is in the form of a tablet.

5. The method of claim 1 wherein the administration is parenteral.

6. The method of claim 1 wherein the alkyl group is selected from the group consisting of methyl, ethyl, propyl, butyl, pentyl, hexyl, isopropyl, isobutyl, sec-butyl, t-butyl, isopentyl, amyl, t-pentyl, cyclopentyl, and cyclohexyl.

7. The method of claim 1 wherein the acyl group is selected from the group consisting of acetyl, propionyl, butyryl, pentanoyl, 3-methylbutyryl, hydrogen succinate, 3-chlorobenzoate, benzoyl, acetyl, pivaloyl, mesylate, propionyl, valeryl, caproic, caprylic, capric, lauric, myristic, palmitic, stearic, and oleic.

8. A method for the treatment of HBV infection in a human or other host animal, comprising administering an HBV treatment amount of the nucleoside of claim 2 in alternative dosages with a compound selected from the group consisting of the (−)-enantiomer or racemic mixture of 2-hydroxymethyl-5-(5-fluorocytosin-1-yl)-1,3-oxathiolane; the (−)-enantiomer or racemic mixture of 2-hydroxymethyl-5-(cytosin-1-yl)-1,3-oxathiolane; an enantiomer or racemic mixture of 2'-fluoro-5-iodo-arabinosyluracil (FIAU); an enantiomer or racemic mixture of 2'-fluoro-5-ethyl-arabinosyluracil (FEAU), carbovir, or interferon.

9. A method for the treatment of HBV infection in a human or other host animal, comprising administering an HBV treatment amount of the nucleoside of claim 1 combination with a compound selected from the group consisting of the (−)-enantiomer or racemic mixture of 2-hydroxymethyl-5-(5-fluorocytosin-1-yl)-1,3-oxathiolane; the (−)-enantiomer or racemic mixture of 2-hydroxymethyl-5-(cytosin-1-yl)-1,3-oxathiolane; an enantiomer or racemic mixture of 2'-fluoro-5-iodo-arabinosyluracil (FIAU); an-enantiomer or racemic mixture of 2'-fluoro-5-ethyl-arabinosyluracil,(FEAU), carbovir, or interferon.

10. The method of claim 1 wherein the nucleoside is selected from the group consisting of β-L-2',3'-dideoxycytidine (β-L-FddC), β-L-2',3'-dideoxy-5-fluorocytidine (β-L-ddC), and (+)-β-D-2-hydroxymethyl-5-(5-fluorocytosin-1-yl)-1,3-dioxolane ((+)-β-D-FDOC).

11. The method of claim 1, wherein the nucleoside is selected from the group consisting of β-L-2',3'-dideoxycytidine (β-L-FddC), β-L-2',3'-dideoxy-5-fluorocytidine (β-L-ddC), and (+)-β-D-2-hydroxymethyl-5-(5-fluorocytosin-1-yl)-1,3-dioxolane ((+)-β-D-FDOC).

* * * * *